United States Patent

Koren

Patent Number: 5,971,916
Date of Patent: Oct. 26, 1999

[54] VIDEO CAMERA COVER

[76] Inventor: Arie Koren, P.O. Box 8288, Industrial Area, South Netanya, Israel

[21] Appl. No.: 08/866,408

[22] Filed: May 30, 1997

Related U.S. Application Data

[63] Continuation of application No. 08/578,150, Dec. 27, 1995.
[51] Int. Cl.$^6$ ........................................ A61B 1/04
[52] U.S. Cl. ......................... 600/122; 600/121; 359/510
[58] Field of Search .................................. 600/121, 122, 600/123, 124, 125; 359/510, 507, 511; 206/363, 438, 440, 69, 828

[56] References Cited

U.S. PATENT DOCUMENTS

| | | | |
|---|---|---|---|
| 4,914,521 | 4/1990 | Adair | 128/6 X |
| 5,078,483 | 1/1992 | Herzberg | 359/510 |
| 5,301,657 | 4/1994 | Lafferty et al. | 128/6 |
| 5,325,846 | 7/1994 | Szabo | 128/4 |
| 5,363,843 | 11/1994 | Danshevar | 600/122 X |

FOREIGN PATENT DOCUMENTS

WO 90/15569  12/1990  WIPO ................. 600/122

*Primary Examiner*—Beverly M. Flanagan

[57] ABSTRACT

Expendable video camera cover for medical use comprises a sleeve-shaped cover means shaped such as to cover a video camera and its electrical cable, and rigid ring-shaped case means for holding the cover means therein. The case has a generally U-shaped cross-section with its outer and lateral sides closed and leaving a central hole open, and the cover means is contained in said case in a tightly packed state resulting from the cover means having, first, one of its ends fixedly attached to said case, and second, the rest of the cover means being gradually crushed against the outer and lateral sides of the case means such as to leave a central hole in the cover means in its packed state, and leaving the second end of the cover means free. A process for manufacturing a video camera cover comprises the steps of attaching one side of a sleeve-shaped cover means to a rigid case; inserting the rigid case with one end of the cover means attached thereon to a pole mounted on a base, so that the cover means can be inserted into the case; and gradually crushing said cover means into that case.

1 Claim, 4 Drawing Sheets

VIDEO CAMERA COVER

CROSS-REFERENCES TO RELATED APPLICATIONS

This is a continuation to my prior nonprovisional application, Application Ser. No. 08/578,150 filed Dec. 27, 1995 with the U.S. PTO, for VIDEO CAMERA COVER, now abandoned. This is a file wrapper continuation pursuant to 37 C.F.R. 1.62.

The application Ser. No. 08/578,150 is to be abandoned upon granting the benefit of filing date of the parent to the present application.

BACKGROUND OF THE INVENTION

This invention relates to video camera covers, and more particularly to such covers which are sterile and include means for covering video cameras for medical use.

Heretofore, various devices and methods have been devised to sterilize the video cameras used in operation rooms or for other medical purposes. Medical equipment may be sterilized by the use of chemical or physical agents, for example using hot steam, gas or gamma rays sterilization. These means may not be appropriate for the delicate video camera.

A more convenient sterilization means uses expendable sterile covers wrapped around the medical equipment. The expendable cover or drape is used only once; it is removed and thrown away after use. Until now, it was difficult to cover the video camera and cable, since a long sleeve is required (about 250 cm or more). It takes time to unwrap the sleeve; handling the long sleeve during the covering process may be difficult. Moreover, special care has to be paid so that no part of the sleeve should touch any nonsterile surface, for then the sleeve is no more sterile and does not protect the patient or the medical staff. Sterile covers known in the art are folded to a bulky package, which is difficult to store and to handle.

For example, Adair Edwin, U.S. Pat. No. 5,433,221, details a windowed self-centering drape for a surgical camera. The drape includes a generally cylindrical body portion and a flexible and elastic distal end. The proximal end of the body portion may include either a roll fold or an accordion fold in order to reduce the size of the drape for storage prior to use.

Lemke Norbert, U.S. Pat. No. 5,419,313, details a microwave sterilizable and reusable endoscope which has an objective arranged at its distal end, the image of which a relay-lens system conveys to the proximal end of the endoscope a light guide at least partially surrounds the relay-lens system and the objective, and conveys illumination light of an illumination light source from a light-entry connection to the distal end. The light guide is provided with a hollow-cylinder made of a transparent and optically clear material which surrounds the objective and the relay-lens system. The light from the illumination light source can be coupled into the circular front face of the hollow cylinder.

Szabo Steve, U.S. Pat. No. 5,325,846, details an endoscopic draping apparatus and method which allows operating room personnel to easily and expeditiously drape an endoscope. The drape is preferably made of polyethylene or some other suitable plastic material. The cylindrical drape cartridge itself acts as a shroud and functions as a sterile barrier. The drape cartridge consists of an inner and outer polyethylene tube which retains the polyethylene drape within its walls. The proximal end of the cartridge is mechanically secured by detents and a chamfer that encase a corrugated pattern of the polyethylene drape. The inner tube acts as a mandrel, allowing the drape to be compressed in a manner that accommodates the various lengths of required draping while lessening the bulk of the draping system.

Lafferty et al, U.S. Pat. No. 5,301,657, detail a disposable sterile sleeve which is removably attachable to a video camera of an arthroscope. The sleeve comprises a flexible elongate tubular shroud and a rigid annular mounting collar. The shroud is open ended with the collar rotatably attached to one open end by a connector member providing independent rotation of the collar relative to the shroud. A pull tab is attached to the opposite open end of the shroud to facilitate extension of the shroud over the camera. The sleeve may be compacted for storage prior to use by tightly scrunching the shroud together, thereby folding it onto itself. To attach the sleeve to the camera, the video camera is inserted through the compacted shroud until it engages the collar. A male thread provided on the camera is threaded into a female thread provided on the collar and the shroud is then extended over the camera by pulling on the tab to draw out the folds in the shroud.

Dunn James, U.S. Pat. No. 5,274,500, details a surgical drape for an endoscopic video camera device which provides a sealed, sterile encasement of the camera and its associated transmission cable and which permits quick, easy interchanging of various endoscopic rod lenses without contamination of the camera head or cable or distortion of the camera image. More particularly, it is concerned with a drape having an opening for insertion of a camera and cable, a clear lens, and structure for constricting the drape around the camera and cable.

Adair Edwin, U.S. Pat. No. 5,251,613, details a videoscope which can easily be used by the doctor to examine the cervix and vagina for cancerous lesions or other abnormalities. The video camera unit can be removed from the speculum and inserted into a sterile sheath for reinsertion into the vagina for examination for lesions and areas covered by the speculum blade. It can also be inserted into the colon and other body passageways where lesions are suspected. The video camera unit can be removed from the sheath, resterilized or disinfected and reattached to a sterile speculum for use with another patient.

Hicks John, U.S. Pat. No. 5,198,894, details an endoscope having a sleeve-like drape secured in a retracted position at the proximal end of the endoscope. The proximal end of the endoscope is secured to a CCD camera, the drape is extended to telescope over and envelope the camera such that the resulting outer surface of the drape in its extended position remains sterile.

Kurtzer Stephen, U.S. Pat. No. 5,168,863, details an apparatus for providing a sterile operating environment for endoscopic diagnosis and/or surgery. A covering comprises a pair of generally orthogonally arranged component bags. Each of the component bags is of an accordian-like extendible type. The component bags are joined adjacent the open end of one bag and an aperture adjacent the open end of the other bag. The open end of the second bag is engaged either to a sterile endoscopic probe preferably of the disposable type or to a shield for enclosing the distal end of an endoscope. The entire apparatus is sterilized and configured so that the component bags can be extended along the camera and light guide cables of the endoscopic system so that resistant spores, bacteria and viruses cannot contaminate the open incision.

Disadvantages of these devices and methods include the difficulty in covering the video camera and the bulky package.

SUMMARY OF THE INVENTION

According to the present invention, there is provided an expendable device to cover or drape video cameras and their electrical cable, to achieve better infection control. Infection control is meant to include infection protection and infection prevention as known in the art.

The camera and its cable are sterilized by covering them with a sterile cover, that is the expendable device described in the present invention. Thus, the cover separates between the personnel and patient on one side, and the camera and its cable on the other side.

According to one aspect of the present invention, there is provided a sterile sleeve-shaped cover which is packed into a hollow, rigid ring to form a compact package and to protect the sleeve from mechanical damage.

According to a second aspect of the present invention, the cover is packed such as to retain a central hole, to facilitate the insertion of the video camera therein, for easy camera covering.

According to a third aspect of the present invention, the ring containing the sterile cover has a central hole, to enable the cover to be taken out at either side.

According to a fourth aspect of the present invention, the cover is contained in the ring such as to allow it to be taken out gradually, as the video camera and cable are covered. This provides for ease of use and protects the sleeve from contamination.

Further objects, advantages and other features of the present invention will become obvious to those skilled in the art upon reading the disclosure set forth hereinafter.

DESCRIPTION OF THE PREFERRED EMBODIMENTS

A preferred embodiment of the present invention will now be described by way of example and with reference to the accompanying drawings.

The expendable device described in the present invention is used to sterilize a video camera and its cable, by covering them with a sterile sleeve-shaped cover. Although the inside surface of the cover becomes contaminated from coming into contact with the unsterile camera and cable, the outer surface of the cover remains sterile. Thus, the cover separates between the personnel and patient on one side (the outer, or sterile side), and the camera and cable on the other side (the inner, or unsterile side). The camera and cable thus covered can be touched by personnel and patient, without danger of contamination.

Figure 1:
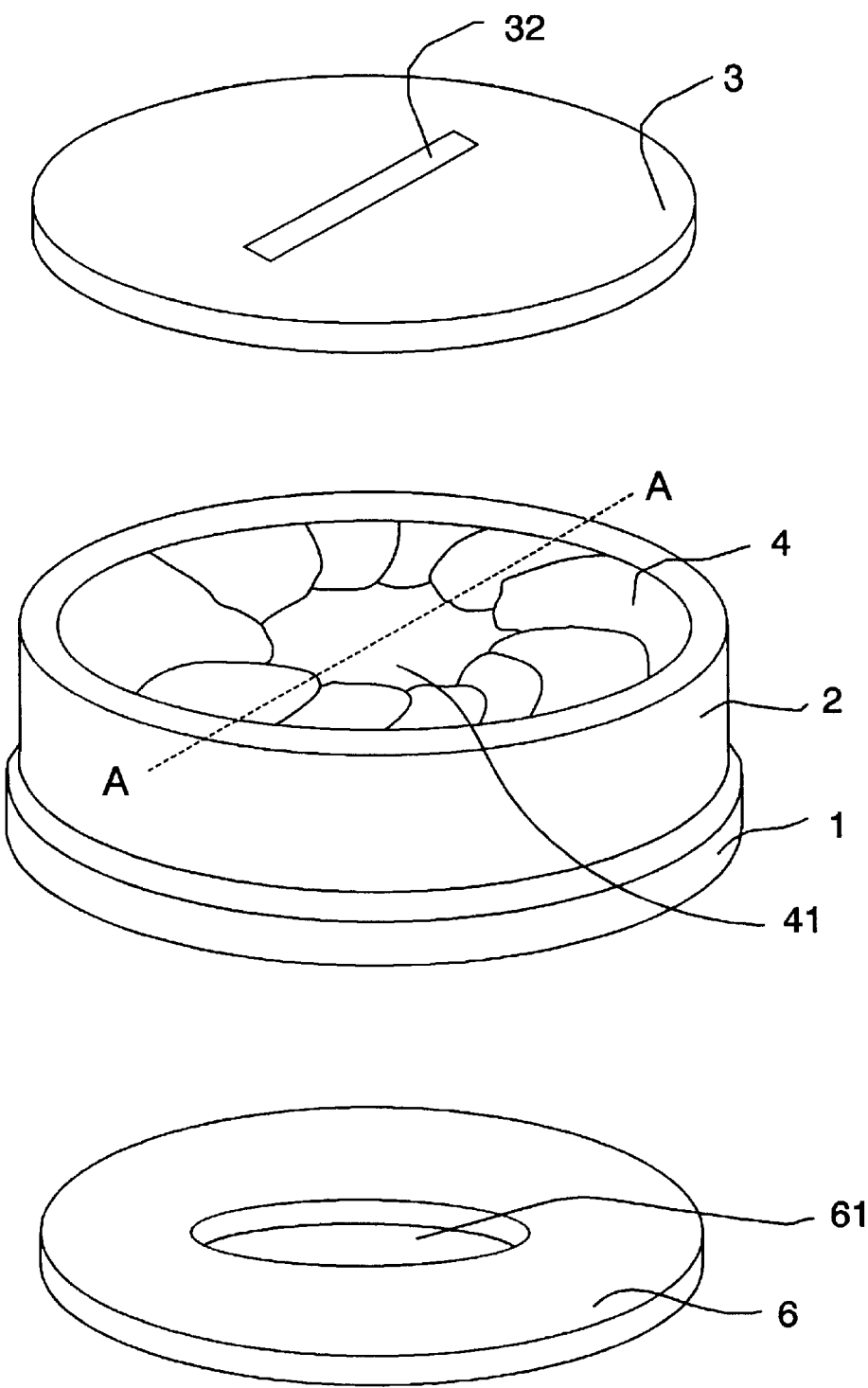
FIG. 1 illustrates the structure of the sterile video camera cover.

Referring to FIG. 1, an example of a sterile video camera cover, the drawing details a complete, assembled device with upper cover 3 removed. The rigid ring is made of outer part 1 and inner part 2, which are inserted into each other to form the ring having an U-shaped cross-section, that is the body of the ring is closed on three sides (the upper, the lower and the lateral sides) and remains open at the fourth, or inner side. Sterile sleeve 4 is crushed inside the ring made of parts 1 and 2 and contained therein. Upper cover 3 is inserted into the ring as well, to prevent sleeve 4 from coming out of the ring. One end of sleeve 4 is attached to the ring, preferably between parts 1 and 2. This provides for a reliable mechanical attachment, without glue or other process being used. The other end of sleeve 4 is inserted into slit 32 in upper cover 3 and attached thereto.

The process of inserting sleeve 4 into the ring, to be detailed below, leaves hole 41 in the packed sleeve 4. Hole 41 in the center of the device is formed by inserting sleeve 4 into the ring-shaped case formed by parts 1 and 2 in such a way as to crush sleeve 4 outwards against that case, using a method further detailed below. This is the sleeve 4 in its packed state. A cross-sectional view further detailing hole 41 is included in FIG. 3. Hole 41 is used to insert the video camera (not shown) therein. The camera can be inserted into sleeve 4 from either side, after removing cover 3. Upper cover 3 is made of cardboard or plastic. Cardboard is preferred, since it can be easily taken off or ripped off, to allow easy access to sleeve 4.

It is essential, in order to achieve the desired sterilization effect, to keep at all times a complete separation between the outer (sterile) surface of the sleeve or cover, and the inner (nonsterile) surface. Otherwise, that is if the outer surface comes into contact with the video camera or its electrical cable, then that outer surface becomes contaminated (is no longer sterile) and may endanger the patient. The patient may then become contaminated either directly, by touching the contaminated surface, or indirectly through one of the medical team who may become contaminated and later transfer the bacteria to the patient.

That extremely important separation between the outer surface and the inner surface is achieved reliably and automatically in the present invention, being an inherent property of the structure which has one end of the sleeve free, and the other fixedly attached to the outer ring. The use of the camera cover is detailed below, with reference to FIG. 3. Here there are explained the implications of the cover structure on the sterilization thus achieved.

Suppose the camera (not shown) is inserted into the ring from the right side, then is taken out to the left, with the cable following. Suppose that, prior to inserting the camera, the sleeve had its free end inside the ring. The opening at the end of the sleeve is the border between the two surfaces of the sleeve: one surface of the sleeve (to be called the left side surface, since it is to the left of the opening) and the other surface of the sleeve (to be called the right side surface).

After inserting the camera from the right, the right side surface of the sleeve becomes the inner surface, which cames into contact with the camera and cable, and becomes contaminated. The left side surface of the sleeve becomes the outer surface, and remains sterile. As more and more of the sleeve unfolds out of the ring, the left surface never comes into contact with camera or cable, and remains sterile as desired.

If the camera is inserted from the left, the same result is achieved, only the surfaces of the sleeve change roles: now the left side surface becomes the inner surface and is contaminated, whereas the right side surface becomes the outer surface of the cover and remains sterile.

That result could not be achieved where both ends of the sleeve are free during the covering process. In that case, according to the order in which the sleeve unfolds, various parts of the sleeve may become the inner surface or the outer surface, and may change roles in the process. If a part of the sleeve which came into contact with camera or cable later becomes the outer surface, then the outer surface of the sleeve is no more sterile and the cover would not achieve its sterilization goal.

Since sleeve 4 is tightly packed into the ring, a small package is achieved, for example an about 250 cm long and 15 cm wide sleeve can be packed into a ring of about 10 cm diameter and 3 cm width.

Optional lower cover 6 is added to better protect sleeve 4 and keep it inside the ring. Cover 6 is inserted between part 1 and sleeve 4 to be mechanically held therebetween. Cover 6 has a hole 61 of a diameter about equal to the diameter of hole 41 in sleeve 4.

The diameter of hole 41 is about 3 cm, corresponding to the diameter of the pole used to insert the cover, as detailed below with reference to FIG. 4(B).

The small width of the ring, about 3 cm, allows it to be handled easily, using one hand, for covering the video camera cable.

Figure 2:
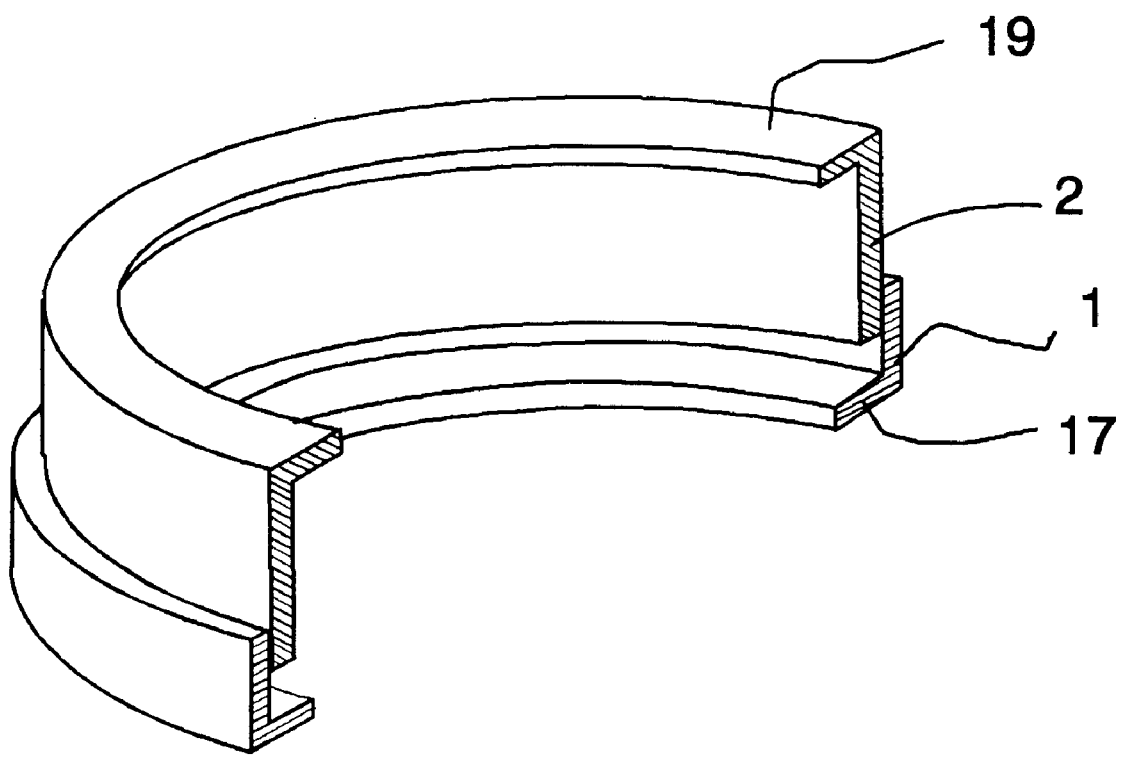
FIG. 2 details the structure of the rigid hollow ring.

FIG. 2 is a cross-section view of the ring, showing outer part 1 and inner part 2. Upper part 19 and lower part 17 serve to hold the sleeve 4 (not shown) inside the ring, and to hold upper cover 3 (not shown here) as well. In a preferred embodiment, only the upper cover is required, because of the method of inserting sleeve 4 into the ring, as detailed below.

Figure 3:
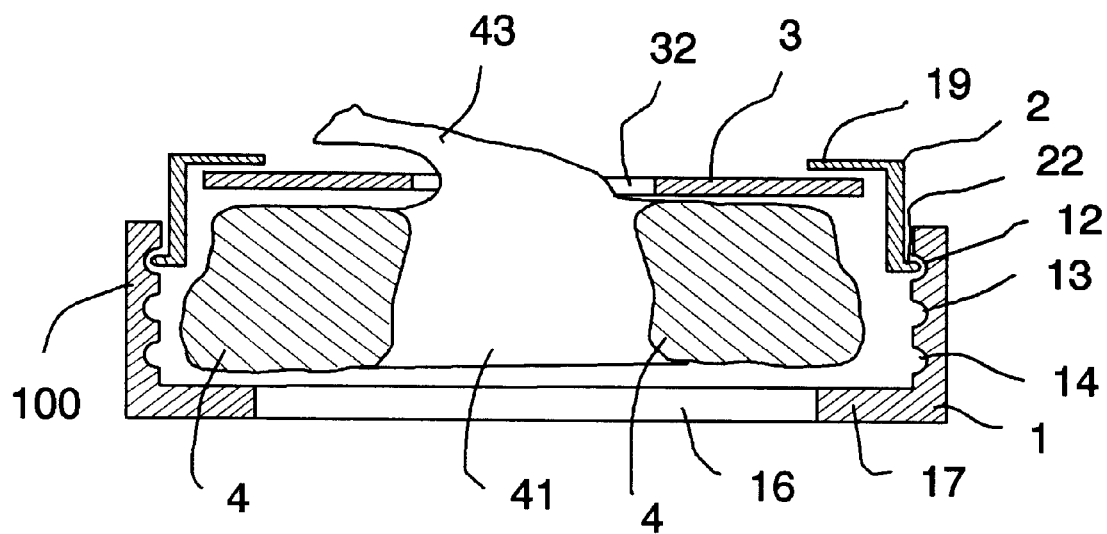
FIG. 3 is a cross-sectional view of the ring containing the sterile cover.

FIG. 3 is a cross-section view of the complete assembled device. The hollow ring is formed between inner part 2 and outer part 1. Outer part 1 has several grooves 12, 13, 14 in its inner side, which complement protruding edge 22 of inner part 2, thus allowing to reliably fix part 1 to part 2 when edge 22 rests in one of grooves 12, 13, 14. Several grooves are required to form a ring having one of several possible width dimensions, corresponding to one of several desired sleeve 4 lengths each. In case the hollow ring is intended to contain only one type of sleeve 4 having a fixed predefined length, then only one groove 12 is required on the outer part 1 of the ring. In that case, groove 12 is made at such a location that, when parts 1 and 2 are assembled together, the width of the resulting ring is such as to be capable of containing the sleeve 4 having that predefined length therein.

One end of sleeve 4 is held between parts 1 and 2, being reliably fixed between edge 22 and one of grooves 12, 13, 14. Other end 43 of sleeve 4 remains free, and is passed through slit 32 in cover 3. Cover 3 is inserted between packed sleeve 4 and upper side 19 of the ring. Ring 100 comprises parts 1 and 2 mounted together as detailed above, or another embodiment using one part ring.

Hole 41 in the center of the device is a result of the sleeve 4 being inserted into ring 100 by crushing it outwards, towards the left and right sides of ring 100 as shown; actually the device has a circular symmetry, with sleeve 4 being shaped as a ring and contained in ring 100 and closely adhering to its outer wall.

The distance between the components was exaggerated, to clearly illustrate each part; actually sleeve 4 is tightly pressed against parts 1 and 2 of the ring and against cover 3, without much empty spaces therebetween. Similarly, edge 22 rests tightly in one of grooves 12, 13, 14, with no empty spaces left.

Figure 4:
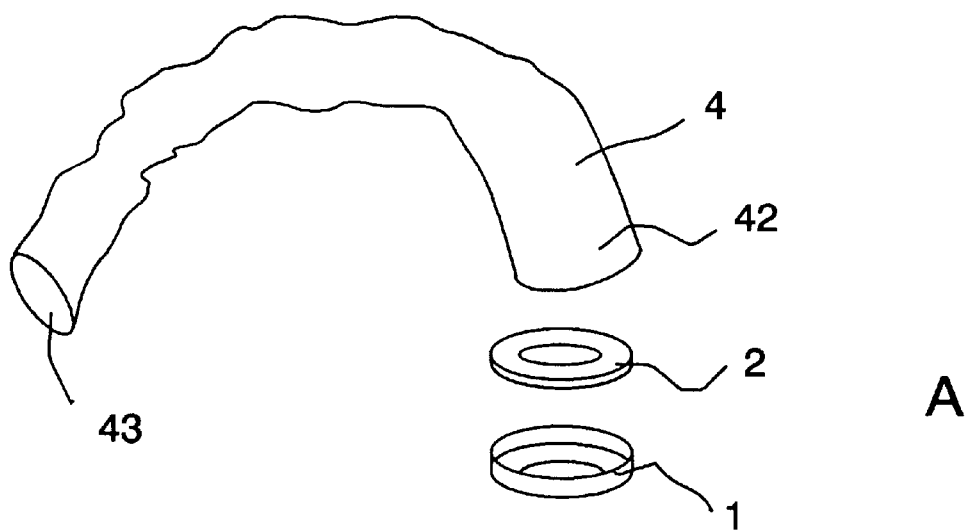
FIG. 4 illustrates the device and process for inserting the sterile cover into the ring.
Figure 4:
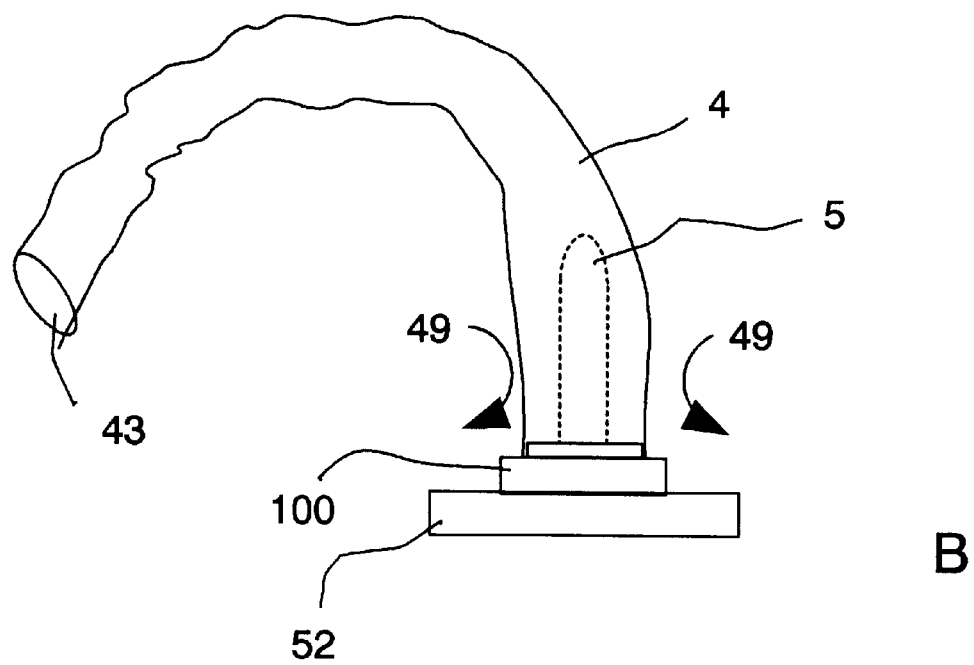

FIG. 4 illustrates the device and process for inserting a sterile sleeve-shaped cover 4 into the ring. Referring to FIG. 4 (A), end 42 of sleeve 4 is put so as to enclose part 2 of the ring. Outer part 1 is then attached to inner part 2 so as to fix end 42 therebetween. Other end 43 of sleeve 4 remains free.

Referring to FIG. 4(B), the ring containing end 42 of sleeve 4 is put in a sleeve insertion device comprising pole 5 and base 52. Pole 5 has a rounded end so as not to damage sleeve 4 during insertion.

The insertion process consists in holding part of sleeve 4 which is wrapped around pole 5 and pushing it down and sideways as detailed by arrows 49, such that the sleeve is pushed inside ring 100. Ring 100 comprises parts 1 and 2 mounted together or another embodiment using one part ring. A length of about 10 cm of sleeve 4 is being pushed inside ring 100 each time.

The abovedetailed process is repeated until the whole length of sleeve 4 is inside ring 100, with only sleeve end 43 remaining free, out of ring 100. This special procedure results in sleeve 4 being tightly packed inside ring 100, to occupy a small volume. Pole 5 helps sleeve 4 to become packed in an efficient structure, while leaving a central hole in the packed sleeve. Pole 5 has a preferred length of about 40 cm and diameter of 3 cm.

There is no regular folding of sleeve 4, but sleeve 4 arranges itself in the most efficient manner while being crushed between ring 100 and pole 5. This results in sleeve 4 being packed in a small volume of ring 100, as detailed above.

This structure and method result in sleeve 4 being easily taken out of ring 100, it unfolding the same way as during insertion, on the reverse. To use the video cover, ring cover 3 (FIG. 3) is taken out of ring 100, then the endoscope or optics (not shown) is inserted into end 43 of sleeve 4. The endoscope can be inserted from either side of ring 100. Cover 3 can be removed or cut off. Sleeve 4 is then unfold gradually from inside ring 100, to cover the video camera and its attached electrical cable to achieve a sterilized camera. This results in an easy and fast unfolding of sleeve 4, without wasting time to open the package or check the right direction or unfold the cover according to a predefined procedure.

As sleeve 4 unfolds gradually out of ring 100, it covers the camera and its cable. The inner surface of sleeve 4, which becomes contaminated from the contact with the camera and cable, is kept separated from the outer surface of sleeve 4, which remains sterile. The structure of the device as detailed, wherein one side of sleeve 4 is attached to the ring 100 and the sleeve is crushed inside ring 100, results in the sleeve 4 being held inside ring 100 while it gradually unfolds out, as the user holds ring 100 and moves it along the camera and its cable to gradually cover them.

Sleeve 4 packed in ring 100 tends to exit upwards, with the lower part, that which was close to base 52, being tightly held in itself. Thus, a cover is required only for the upper side of ring 100, to prevent sleeve 4 from springing out of ring 100. A second, optional cover can be put on the lower side of the ring as well, to better protect sleeve 4 inside.

Optional lower cover 6 (see FIG. 1) may be inserted into part 1 of the ring prior to inserting sleeve 4 into the ring. Cover 6 then helps guide sleeve 4 during insertion and provides better protection for sleeve 4 after insertion.

Another embodiment (not shown) disposes of cover 6 by using part 1 with inner hole of about the same size as hole 41.

To serve as a sterile cover, the complete device comprising ring 100 with sleeve 4 packed therein and cover 3 attached thereon undergoes sterilization and is packed in a sterile hermetic bag or other package to preserve it sterile until use.

In other embodiments, the ring is made of one piece of plastic or cardboard or metal (not shown). In this case, one end of sleeve 4 is bonded to ring 100 using methods known in the art.

Cases having various shapes can be used to contain sleeve 4 therein, for example a rectangular, triangular, polygonal or other shape case (not shown) with upper and lower holes for sleeve insertion and extraction. Still another method uses folding sleeve 4 onto itself and around guiding pole 5, without rigid external case 100. To prevent sleeve 4 from unfolding, it is mounted in a flexible bag or case which holds it tightly packaged until use.

It will be recognized that the foregoing is but one example of an apparatus and method within the scope of the present invention and that various modifications will occur to those skilled in the art upon reading the disclosure set forth hereinbefore.

What is claimed is:

1. A process for assembling a video camera cover comprising the steps of:

(A) attaching one end of a sleeve-shaped cover means to a rigid case;

(B) inserting said rigid case with one side of said cover means attached thereon to a pole mounted on a base, such as said cover means can be inserted into said case while said pole keeps a central hole therein; and (C) gradually crushing said cover means into said case, while pushing said cover sideways and out, away from the hole in said case which is used to insert said cover means therein.

* * * * *